United States Patent [19]

Murakami et al.

[11] Patent Number: 4,556,689
[45] Date of Patent: Dec. 3, 1985

[54] COMPLEX OF BIOLOGICALLY ACTIVE PROTEIN WITH REACTIVE HIGH POLYMER HAVING BONDED THERETO BIFUNCTIONAL CHELATE

[75] Inventors: Yoshiaki Murakami, Takatsuki; Kunio Shiba, Takarazuka; Akira Yoshitake, Kyoto; Keietsu Takahashi, Itami; Nobuo Ueda, Kawanishi; Masaaki Hazue, Amagasaki, all of Japan

[73] Assignee: Sumitomo Chemical Company, Limited, Osaka, Japan

[21] Appl. No.: 611,117

[22] Filed: May 17, 1984

[30] Foreign Application Priority Data

May 23, 1983 [JP] Japan .................................. 58-91217

[51] Int. Cl.⁴ ...................... C08G 69/48; C08G 69/10; C08G 69/42
[52] U.S. Cl. .................................. 525/54.1; 514/6; 514/21; 514/802; 514/836; 260/112 R; 260/112 B
[58] Field of Search .......................... 525/54.1, 54.11; 424/177; 260/112 R, 112 B; 514/2, 6, 21, 802, 836

[56] References Cited

U.S. PATENT DOCUMENTS 3,927,204 12/1975 Neri et al. ............................ 528/328
4,385,169 5/1983 Kato et al. ............................ 528/328

FOREIGN PATENT DOCUMENTS 0040506 11/1981 European Pat. Off. .
167519 3/1983 Japan .

OTHER PUBLICATIONS

Neri et al., "Synthesis of α,β- Poly[(2-Hydroxyethyl)-DL-Aspartamide], a New Plasma Extender", Jour. Med. Chem., 1973, vol. 16, No. 8, pp.893-897.

Primary Examiner—John Kight
Assistant Examiner—Nathan M. Nutter
Attorney, Agent, or Firm—Stevens, Davis, Miller & Mosher

[57] ABSTRACT

A protein-polysuccinimide complex wherein a biologically active protein is combined with a polysuccinimide having a mean molecular weight of 2,000 to 1,000,000 and consisting of constitutive units represented by the following formulae:

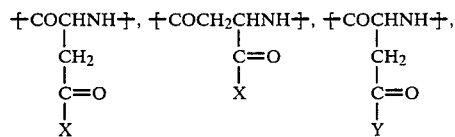

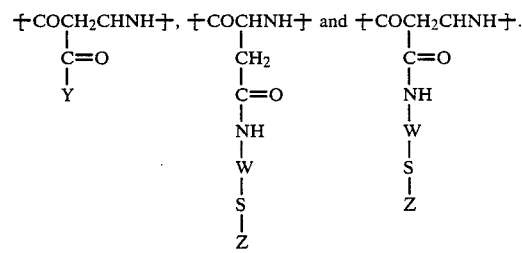

Said complex can be labelled with a radio-metal and can be used as a radioactive diagnostic in the field of nuclear medicine.

13 Claims, No Drawings

COMPLEX OF BIOLOGICALLY ACTIVE PROTEIN WITH REACTIVE HIGH POLYMER HAVING BONDED THERETO BIFUNCTIONAL CHELATE

This invention relates to a reactive high polymer having bonded thereto a bifunctional chelate, a protein-polysuccinimide complex in which said reactive high polymer is bonded to a biologically active protein, a process for preparing the reactive polymer and a process for preparing the complex.

The protein-polysuccinimide complex according to this invention is useful as an intermediate for the preparation of radio-metal ion-labelled diagnostics in the field of nuclear medicine. That is to say, if the biologically active protein is fibrinogen or plasminogen, a diagnostic for thrombus sites can be prepared by binding a radio-metal ion to said protein-polysuccinimide complex. Also, if the biologically active protein is immunoglobulin which can be specifically bound to a specific antigen or its fragment containing antigen-binding sites, a diagnostic for the purpose of the detection of tumor sites can be prepared in a similar manner. Moreover, if the biologically active protein is albumin, blood-pool imaging can be prepared.

It has been attempted in the past to label a biologically active molecule consisting of a proteinous molecule such as fibrinogen with a radioactive substance for the purpose of the detection of a specific disease, for example, the diagnosis of thrombus, and a radio-metal ion which has physical properties suited for nuclear medical diagnosis is used as the radioactive substance.

In this case, there have been attempts to label a biologically active molecule with a radio-metal ion by the use of a bifunctional chelate which can form a chelate with the radio-metal ion and can form a stable chemical bond with the biologically active molecule.

However, if a large amount of the bifunctional chelate is reacted directly with the biologically active molecule for the purpose of increasing the specific radioactivity, the biologically active molecule is susceptible to denaturation. It is, therefore, difficult to obtain a nuclear medical diagnostic having highly specific radioactivity without denaturation of the biologically active molecule by such a conventional method.

The present inventors have conducted extensive research in order to solve the problems mentioned above. As a result, they have found that the above-mentioned problems can be solved by labelling with a radio-metal ion a protein-polysuccinimide complex in which a biologically active protein is bonded to a polysuccinimide derivative [I] consisting of constitutive units represented by the formulae:

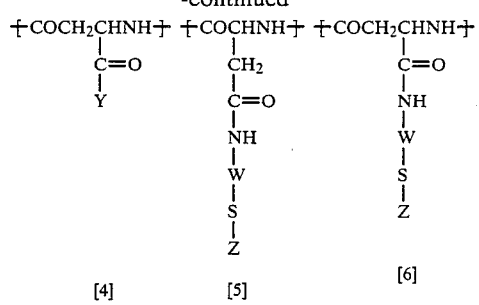

wherein

X represents a residue of a bifunctional chelate having an amino group in the molecule, Y represents a water soluble aliphatic primary amine residue;

W represents a lower alkylene group;

Z represents a hydrogen atom or a group represented by the symbol Z', provided that if Z is a hydrogen atom, the —SZ is a —SH group which can form a —S—S— bond with another —SH group in equilibrium intramolecularly or intermolecularly, and this case is also represented by —SH; and Z' represents a group which can form an active disulfide bond with the adjacent sulfur atom, the respective numbers of constitutive units [1], [2], [3], [4], [5] and [6] in a molecule being n, m, l, r, p and q, respectively, which may denote 0 or natural numbers and have the following relationships;

$n + m \geq 2$ $0.001 \leq (p+q)/(n+m+l+r+p+q) \leq 0.50,$ and the mean molecular weight being 2,000–1,000,000.

The polysuccinimide derivative [I] of this invention (1) can be labelled with a radio-metal ion because it has bonded thereto a bifunctional chelate, and (2) can be combined with a biologically active protein directly or through a crosslinking group by the use of the active part (—SZ) of the polysuccinimide derivative and the —SH group or —NH$_2$ group of the biologically active protein because the polysuccinimide derivative has thiol groups or active disulfide bonds.

As mentioned above, this invention provides a reactive high polymer (polysuccinimide derivative) [I] which is important for the preparation of a radioactive diagnostic, and furthermore, provides a protein-polysuccinimide complex in which said reactive high polymer [I] is bonded to a biologically active protein directly or through a crosslinking group.

In the polysuccinimide derivative [I] according to this invention, the "group which can form an active disulfide bond with the adjacent sulfur atoms" represented by Z' includes, for example, substituted or unsubstituted pyridylthio groups and N-oxides thereof such as 2-pyridyl-thio group

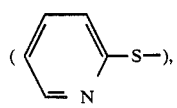

4-pyridylthio group

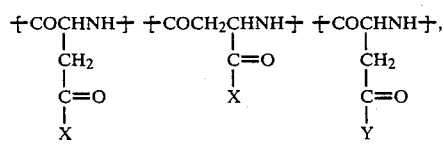

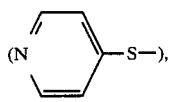

5-carboxy-2-pyridylthio group

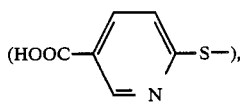

N-oxy-2-pyridylthio group

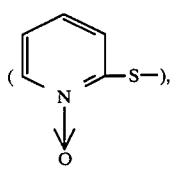

5-nitro-2-pyridylthio group

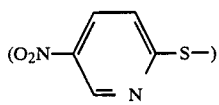

and the like; phenylthio groups having a nitro group such as 3-carboxy-4-nitrophenylthio group

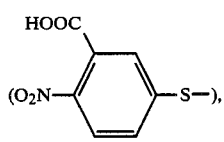

2-nitrophenylthio group

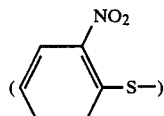

and like; 2-benzothiazoylthio group

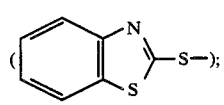

2-benzoimidazoylthio group

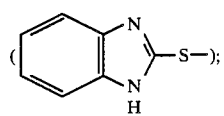

N-phenylamino-N'-phenyliminomethylthio group

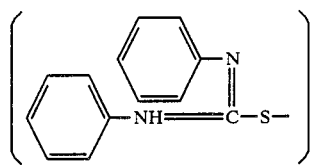

and the like.

The "lower alkylene groups" represented by W includes straight chain or branched chain alkylene groups having 1-4 carbon atoms such as methylene, ethylene, tetramethylene, propylene, 2-methyltrimethylene and the like.

In the "residue of a bifunctional chelate having an amino group in the molecule" represented by X, the "bifunctional chelate" is the terminology used in the field of nuclear medicine, and is the general term of a compound having (1) a functional group having strong chelate forming ability to radio-metal ions, and (2) a functional group which can chemically bond to a biologically active molecule.

(See Radiopharmaceuticals Structure-Activity Relations, by Richard P. Spencer, p. 282).

That is to say, the term "bifunctional chelate containing an amino group" used herein means compounds having a chelate forming ability to various radio-metal ions and also an amide bond-forming ability by the reaction of the amino group in the molecule with a succinimide group

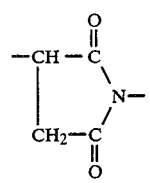

in the polysuccinimide.

In other words, it must have an amino group which can react with the succinimide group to form an amide bond.

Also, the term "bifunctional chelate having an amino group" used herein means to include not only compounds which are, per se, known as bifunctional chelates having an amino group, but also compounds obtained by introducing an amino group into an amino group-free bifunctional chelate.

If the amino group-free bifunctional chelate is, for example, a compound having a carboxyl group, an amino group can be newly introduced into the compound by reacting the carboxyl group with one of the amino groups of a diamino compound (for example, hexamethylenediamine) according to the conventional method.

The specific examples of the "bifunctional chelate having an amino group" include deferoxamine, ethylenediamine-N,N-diacetic acid (EDDA), 1-(p-aminoethyl)phenylpropane-1,2-dione-bis(thiosemicarbazone) and the like which are known as the bifunctional chelates having an amino group, and the bifunctional chelate having an amino group newly introduced thereinto includes those obtained by amino group into diethylenetriaminepentaacetic acid (DTPA), ethylenediaminetriacetic acid (EDTA) and the like.

Among these, deferoxamine and 1-(p-aminoethyl)-phenylpropane-1,2-dione-bis(thiosemicarbazone) are preferred, since they have a stable ligand ability to $^{67}$Ga and $^{99m}$Tc, respectively. It is particularly desirable to use deferoxamine because the labelling amount can be easily increased.

Y is the residue of a water soluble aliphatic primary amine. This residue is introduced for the purpose of improving the water solubility of the reactive high polymer though it is not always necessary for the purpose of this invention (l+r=0). The water soluble aliphatic primary amine used includes aliphatic primary amines having hydroxyl groups such as ethanolamine, 3-amino-1,2-propanediol and the like; aliphatic amines represented by $CH_3(CH_2)_gNH_2$ (g=an integer of 1-4); and the like. Particularly preferred are amines having hydroxyl groups such as ethanolamine, 3-amino-1,2-propanediol and the like.

n+m denotes the number of the constitutive units to which the bifunctional chelate having an amino group is bonded, l+r denotes the number of the constitutive units having bonded thereto a water soluble aliphatic primary amine, and p+q denotes the number of the constitutive units having bonded thereto a thiol group or a group which can form an active disulfide bond with the adjacent sulfur atom.

(n+m)/(n+m+l+r+p+q) denotes the number of mols of condensed X (the condensed bifunctional chelate having an amino group in the molecule) per mol of succinimide group which is a monomer unit.

(p+q)/(n+m+l+r+p+q) denotes the number of mols of the condensed group represented by the formula —NH—W—S—Z per mol of succinimide group which is a monomer unit.

The arrangement of the respective constitutive units [1]-[6] in a polymer is not critical and the polymer may be a random copolymer or a block copolymer.

The molecular weight is 2,000–1,000,000, preferably 5,000–100,000; n+m is 2 or more, (n+m)/(n+m+l+r+p+q) is less than 1, and (p+q)/(n+m+l+r+p+q) is 0.001 or more but 0.50 or less, preferably 0.3 or less.

If the molecular weight is less than the above range, the labelling amount of a radio-metal ion cannot be increased because of the small number of the molecules of the bifunctional chelate bonded to 1 molecule of the reactive high polymer. This is not desirable. If the molecular weight is too large, the excretion of the polymer labelled with a radio-metal ion but not bonded to the biologically active molecule, which may be incorporated or formed by splitting in a living body, becomes slow. This is not desired. The object of this invention of improving the specific radioactivity cannot be achieved, unless n+m is 2 or more.

(p+q)/(n+m+l+r+p+q) is 0.001 or more, and it is not desirable that this ratio be less than the above-mentioned value since the ratio of the biologically active molecule bonded becomes low. It is 0.5 or less, preferably 0.3 or less, and if it is too large, the association of the biologically active molecule is apt to be caused and the amount of insoluble portion and excessively large molecular weight portion is increased. This is not desired.

The polysuccinimide derivative [I] of this invention can be easily derived from a polysuccinimide whose main constituent is the constitutive unit represented by the following formula:

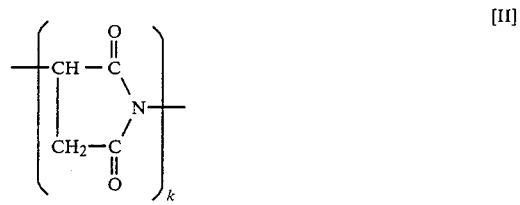

wherein k represents a natural number.

The polysuccinimide is a polymer separately named "anhydropolyaspartic acid", and can be prepared mainly by the thermal condensation of aspartic acid [J. Kovacs et al., J. Org. Chem. 26, 1084 (1961); P. Neri et al., J. Med. Chem. 16, 893 (1973)].

As an example of the preparation method, the polysuccinimide [II] can be obtained by the dehydration polymerization of aspartic acid (which may be an optically active substance or a DL-isomer) under atmospheric pressure or reduced pressure at a temperature of 160° C. or more but 240° C. or less. If the dehydration conditions are severe, a high molecular weight polymer can be obtained in a shorter time, but it is not desirable to make the temperature higher because the decomposition of the polymer results. If the temperature is lower than the above range, a longer time is required to produce the polymer, and hence, such a temperature is not desired.

After completion of the polymerization reaction, the reaction product is dissolved in dimethylformamide (DMF) or dimethylsulfoxide (DMSO) and reprecipitated in water to remove unreacted aspartic acid and condensation products of lower molecular weight. After filtration through a glass filter, the product is dried. If necessary, the above procedure is repeated.

The IR and $^{13}$C-NMR data of the polymer thus obtained suggest that the polymer is represented by the formula [II]. However, it is generally recognized that even if it partially contains other constitutive units, the constitutive unit represented by the formula [II] is substantially the main constituent.

It is known that the polysuccinimide thus obtained reacts with a compound having an amino group, for example, ethanolamine as shown by the following reaction formulas:

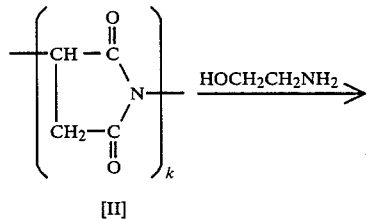

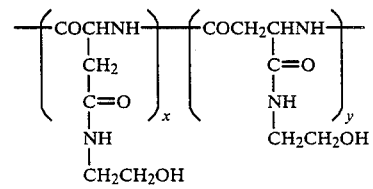

wherein k, x and y denote natural numbers.

In order to obtain the polysuccinimide derivative [I] of this invention, that is, the reactive high polymer having bonded thereto the bifunctional chelate and having a bonding ability to a biologically active molecule, the following methods may be used:

(1) A method comprising reacting polysuccinimide with (a) a bifunctional chelate having an amino group, (b) a compound represented by the formula H$_2$N—W—S—Z (wherein W and Z have the same meanings as defined above) and if necessary, (c) a water soluble aliphatic amine.

(2) A method comprising reacting polysuccinimide with (a) a bifunctional chelate having an amino group, (b) a compound represented by the formula, H$_2$N—W—S—S—R (wherein W has the same meaning as defined above, and R represents a hydrocarbon group such as an alkyl group, for example, a lower alkyl group having 1–5 carbon atoms; an aralkyl group, for example, an unsubstituted or substituted phenyl-C$_1$-C$_3$alkyl group; an aryl group, for example, an unsubstituted or substituted phenyl group; or the like), and if necessary, (c) a water soluble aliphatic primary amine followed by reacting the disulfide of the reaction product with a thiol compound or a borohydride compound to reductively split the disulfide and (3) A method comprising reacting the reactive high polymer of a thiol type (formula [I] in which Z=H) obtained by any of the above methods with a reactive disulfide compound.

Moreover, the above-mentioned methods (1) and (2) include a consecutive reaction method wherein reactions between polysuccinimide and the above-mentioned constituents (a) and (b) and, if necessary, the constituent (c) are consecutively conducted in any sequence and a simultaneous reaction method wherein the reactions of polysuccinimide with a plurality of constituents are simultaneously conducted. Also, if the reaction with the constituent (c) is required, it is possible to take a two-step method wherein the reaction with any one constituent is conducted independently and the reactions with the residual two constituents are conducted simultaneously.

As a reaction solvent, DMF or DMSO which are good solvents for polysuccinimide, is used in the consecutive reactions or the first of the two-step reactions and the simultaneous reaction. The second and subsequent reactions of the consecutive or two-step reactions may be conducted in DMF or DMSO, or when the polysuccinimide derivative obtained by the first or second reaction is water-soluble, the second and subsequent reactions are conducted in water as the solvent.

The reactions with the constituents (a), (b) and (c) in the above-mentioned methods (1) and (2) is conducted by the following procedure:

1 to 30 parts by weight of polysuccinimide or the polysuccinimide derivative having the remaining unreacted succinimide groups

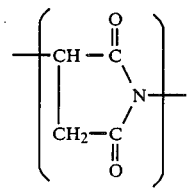

after the first or second reaction is dissolved in 100 parts by weight of DMF, DMSO or water and reacted with one or more of the constituents (a), (b) and (c) to be reacted (0.001–10 mols of each constituent per mol of the succinimide group in the solution) with stirring at −40° to 80° C. for 10 minutes to 20 days. The unreacted constituents can be removed by dialysis or gel-filtration.

The objective polysuccinimide derivative is obtained by lyophilization or by removing the solvent by distillation under reduced pressure.

The amount of the bifunctional chelate and the compound represented by the formula, H$_2$N—W—S—Z (wherein W and Z are as defined above) or the compound represented by the formula, H$_2$N—W—S—S—R (wherein W and R are as defined above), to be introduced can be controlled by previously appreciating the reaction rate with the succinimide group under certain conditions when the reaction is conducted with one constituent, and then determining the concentration of the succinimide group in the aqueous solution, the temperature, the reaction time and the adding amount of the constituents to be reacted. If the reactions with two or more of the constituents are effected simultaneously it is possible by previously appreciating the relative reaction rates of the respective constituents in admixture of 2 or more of the constituents and adjusting the mixing ratio and the adding amounts of the constituents to be added.

The molecular weight is controlled by the selection of the condensation conditions for obtaining the polysuccinimide polymer, and the isolation of the polymer having the intended molecular weight is conducted by the molecular weight fractionation method using the gel-filtration of a DMF solution of the polysuccinimide polymer and the gel-filtration in water as solvent after obtaining the polysuccinimide derivative. It is desirable to conduct the molecular weight fractionation by the gel-filtration in water as solvent after obtaining the polysuccinimide derivative [I].

In order to improve the yield of the molecular weight fractionation, the condensation conditions for obtaining the polysuccinimide [II] are previously selected and the molecular weight fractionation is previously conducted by the gel-filtration of a DMF solution of the polysuccinimide [II].

As an active disulfide compound used in the process for obtaining the reactive high polymer (formula [I] in which Z=Z') having the active disulfide groups by reacting the reactive high polymer of a thiol type (formula [I] in which Z=H) with an active disulfide compound, there are mentioned the disulfide of the group represented by Z' specifically the disulfide of the above-mentioned group illustrated as Z', for example, 2-pyridyldisulfide

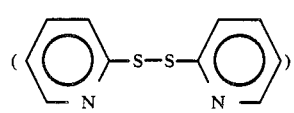

which is the disulfide of 2-pyridylthio group, 4-pyridyldisulfide

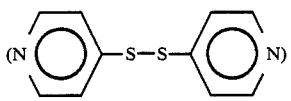

which is the disulfide of 4-pyridylthio group, and 5,5'-dithiobis(2-nitrobenzoic acid)

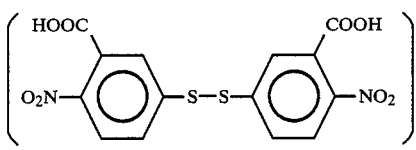

which is the disulfide of 3-carboxyl-4-nitrophenylthio group.

The reaction between the reactive polymer of a thiol type and the active disulfide compound is usually conducted in a uniform reaction system wherein water or an organic solvent such as DMF, DMSO or the like is used as the reaction solvent. It is also possible to carry out the reaction in a reaction system formed by adding the active disulfide compound or an acetone solution or dioxane solution thereof to the aqueous solution of the polymer and mixing them. An appropriate reaction temperature is −5° to 70° C., and reaction time is 1 minute to 24 hours.

In the protein-polysuccinimide complex which is the second object of this invention, the biologically active protein means a protein having a specific accumulation tendency on a specific organ or a specific affection site or a protein exhibiting a specific behavior corresponding to the physiological conditions in a living body, said protein being able to provide information useful for various diagnosis by tracing the behavior thereof in the body. Such a biologically active protein may be not only naturally occurring biologically active proteins per se but also partial decomposition products of said biologically active protein, that is, fragments.

The desirable biologically active protein according to this invention includes, for example, fibrinogen, plasminogen and urokinase which are known to be specifically bound to thrombus sites, and also immunoglobulin which may be specifically bound to a specific antigen such as tumor cell or the like. Moreover, albumin is also included.

Fibrinogen, plasminogen and urokinase are now tried to be used for the diagnosis of thrombus sites, and the diagnosis of tumor sites utilizing the fact that there are many thrombus sites around tumor cells. Fragment E obtained by reacting fibrinogen with thrombin and $Ca^{2+}$ to form a stable fibrin clot and then treating it with plasmin is also known to have a specific binding ability to thrombus sites.

The complex according to this invention in which albumin is used as the biologically active protein can be used for tracing the behavior thereof in blood as a blood pool imaging.

The immunoglobulin includes immunoglobulins obtained by using, as an antigen, a specific protein such as AFP, CEA, HCG and transferrin receptor, using, as an antigen a traget cell such as tumor cell, specific lymphocyte or the like, or using, as an antigen, tissues containing the target cell.

The immunoglobulin can be obtained by subjecting an antiserum separated from an antigen-immunized animal such as a human being, a monkey, a horse, a cow, a goat, a sheep, a rabbit, a guinea pig, a hamster, a rat, a mouse or the like to a usual fractionation such as ethanol precipitation, ammonium sulfate precipitation, ion exchange, gel chromatography or the like. It can be obtained by a method wherein hybridoma is obtained by cancerization of an antibody-producing cell collected from an antigen-immunized animal with a carcinogenic substance or fusion of the antibody-producing cell and a myeloma cell into a hybridoma, followed by recovery of monoclonal antibody produced thereby.

Immunoglobulin has a specific binding ability to an antigen even after its Fc portion has been removed. In general, if immunoglobulin is decomposed with a protease such as papain, trypsin, chymotrypsin, plasmin or the like, a so-called Fab fragment, which has one antigen-binding site, is obtained, and if it is decomposed with pepsin or trypsin under specific conditions, a so-called F(ab')2 fragment, which has two antigen-binding sites, is obtained.

If immunoglobulin is subjected to reduction treatment with dithiothreitol, mercaptoethanol or the like, a monomer having a mercapto group is obtained. If F(ab')2 is similarly subjected to reduction treatment, Fab' having a mercapto group can be obtained.

The bonding of the polysuccinimide derivative and the biologically active protein may be conducted by any known method, for example, the methods mentioned below.

The first method comprises reacting a biologically active protein having a mercapto group, for example, mercaptoalbumin or a monomer or Fab' obtained by reduction of an immunoglobulin or its fragment, F(ab')2, with dithiothreitol or mercaptoethanol, with the reactive high polymer represented by the formula [I] in which Z=Z' by utilization of the mercapto group of said protein or the mercapto group introduced into the amino group of a biologically active protein through a crosslinking group.

As the crosslinking agent for introducing a mercapto group into the amino group of a biologically active protein, through a crosslinking group, many crosslinking agents have already been known. The crosslinking agent in this invention may be any of such known crosslinking agents, and there may be used a compound represented by the formula,

   [IIIa]

wherein $L_1$ represents a bivalent organic group and $Q_1$ represents an alcohol residue of an imide ester, or a salt thereof (for example, HCl salt, HBr salt or the like).

The organic group represented by $L_1$ in the above-mentioned formula [IIIa] includes linear chain or branched chain alkylene groups having 2–6 carbon atoms such as ethylene, trimethylene and the like; and the alcohol residue represented by $Q_1$ includes alkoxy groups having 1–3 carbon atoms such as methoxy, ethoxy and the like. More specifically, the above-mentioned crosslinking agent [IIIa] includes, for example, methyl 3-mercaptopropylimidate hydrochloride

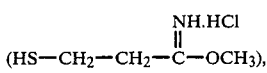

methyl 4-mercaptobutylimidate hydrochloride

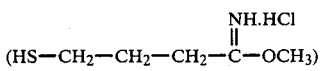

and the like.

Also, 2-iminothiolactone

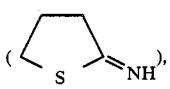

N-acetylhomocystein thiolaclone

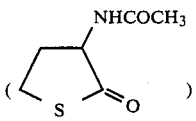

and the like may be used as the crosslinking agent.

Moreover, as the crosslinking agent, there may be used a compound represented by the formula,

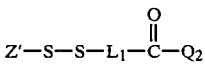 [IIIb]

wherein Z' and $L_1$ have the same meanings as defined above, and $Q_2$ represents an alcohol residue of an active ester, a compound represented by the formula,

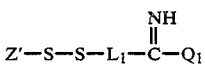 [IIIc]

wherein Z', $L_1$ and $Q_1$ have the same meanings as defined above, or a salt thereof (for example, HCl salt, HBr salt or the like), a compound represented by the formula,

 [IIId]

wherein $L_1$ and $Q_1$ have the same meanings as defined above, or a salt thereof (for example, HCl salt, HBr salt or the like, a compound represented by the formula,

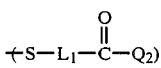 [IIIa]

wherein $L_1$ and $Q_2$ have the same meaning as defined above, S-acetylmercaptosuccinic anhydride

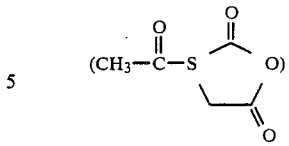

or the like. In this case, a mercapto group can be introduced into a biologically active protein through the crosslinking group by reacting the amino group of the biologically active protein with a crosslinking agent and then reducing the reaction product with a reducing agent such as dithiothreitol or mercaptoethanol or treating it with an alkali.

The crosslinking agent represented by the abovementioned formula [IIIb] includes, for example, N-succinimidyl 3-(2-pyridylthio)propionate

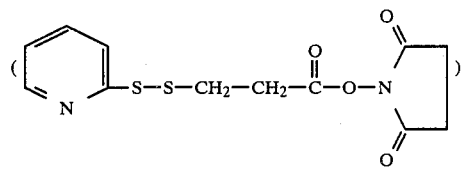

and the like; the crosslinking agent represented by the formula [IIIc] includes, for example, 3-(4'-dithiopyridyl)mercaptopropioimidate hydrochloride

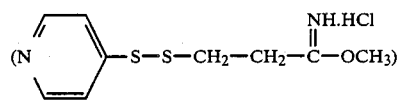

and the like; the crosslinking agent represented by the formula [IIId] includes, for example, dimethyl 3,3'-dithiobispropionimidate hydrochloride

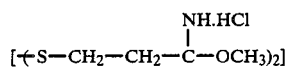

and the like; and the crosslinking agent represented by the formula [IIIe] includes, for example, dithiobis(succinimidylpropionate)

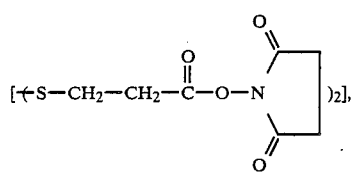

disuccinimidyl-N,N'-diacetylhomocystine

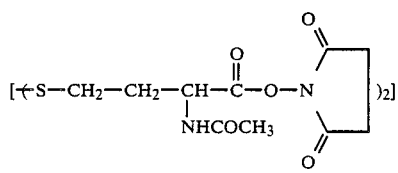

and the like.

The second method comprises first introducing a Z' group into the mercapto group of a biologically active protein having a mercapto group to form a —SZ' group or introducing a —SZ' group into the amino group of a biologically active protein, and then reacting the —SZ' group with a reactive high polymer [I] wherein Z is a hydrogen atom.

The method for introducing a —SZ' group into a biologically active protein includes a method comprising reacting a biologically active protein having a mercapto group with an active disulfide compound or reacting a biologically active protein having a mercapto group introduced to the amino group through a crosslinking group (see the first method mentioned above) with an active disulfide compound, and a method of directly introducing a —SZ' group through a crosslinking group by reacting the amino group of a biologically active protein with a crosslinking agent represented by said formulae [IIIb] or [IIIc].

The third method comprises combining a biologically active protein or a biologically active protein having a mercapto group introduced into the amino group through a crosslinking agent with a polysuccinimide derivative [I] wherein Z is a hydrogen atom through a crosslinking agent by utilizing the mercapto group of a biologically active protein having a mercapto group or the mercapto group introduced to the amino group of a biologically active protein through a crosslinking group. As the crosslinking agent, there are used bifunctional crosslinking agents which can react with a mercapto group.

The bifunctional crosslinking agent which is appropriate to this object and which can react with a mercapto group includes, for example, benzoquinone, a dimaleimide compound represented by the formula,

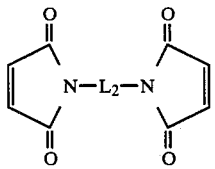
[IV]

wherein $L_2$ represents a divalent organic group, or the like.

The divalent organic group represented by $L_2$ includes, for example, a phenylene group, an azobenzenediyl group, an alkylene group having an oxygen atom in its chain represented by the formula —(CH$_2$)$_{a1}$—O—(CH$_2$)$_{a2}$—, wherein $a_1$ and $a_2$ represent integers of 1–3, and the like.

More specifically, the maleimide compound includes N,N'-(1,2-phenylene)dimaleimide

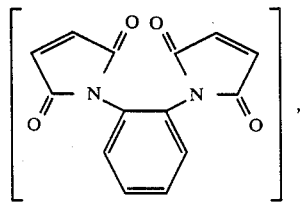

N,N'-(1,4-phenylene)dimaleimide

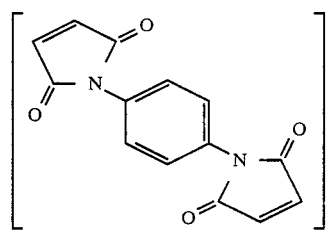

4,4'-bis(maleoylamino)azobenzene

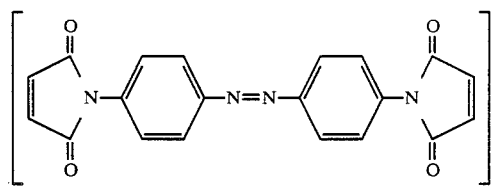

bis(N-maleimidomethyl) ether

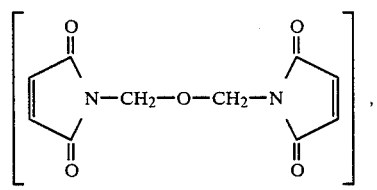

and the like.

In order to combine a biologically active protein with a polysuccinimide derivative [I], one of (1) a biologically active protein having a mercapto group or a biologically active protein having introduced thereto a mercapto group and (2) a polysuccinimide derivative [I] wherein Z is a hydrogen atom, is reacted with a crosslinking agent in excess of the mercapto group contained therein and thereafter the other is reacted with the crosslinking agent.

The fourth method comprises introducing a functional group into a biologically active protein through a crosslinking group by the use of the amino group of the biologically active protein, and then reacting the reaction product with a polysuccinimide derivative [I] wherein Z is a hydrogen atom.

The functional group which can react with a mercapto group includes a maleimide group represented by the formula,

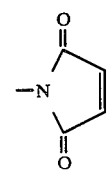

a halogenated methyl group represented by the formula,

—CH$_2$L wherein L represents a halogen atom, and the like. Said halogen atom includes chlorine, bromine and iodine atoms, of which the iodine atom is preferred.

Crosslinking agents used for introducing a functional group into the amino group of a biologically active protein through a crosslinking group are already known, and preferred are compounds represented by the formula, $$[V]$$

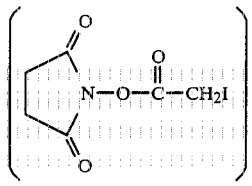

wherein $L_3$ represents a divalent organic group, and $Q_2$ has the same meaning as defined above. In this case, the divalent organic group includes a phenylene group, a group represented by the formula, —$(CH_2)_b$—A— wherein A represents a phenylene group or a cycloalkanediyl group having 5–7 carbon atoms, and b represents an integer of 1–3, an alkylene group having 2–6 carbon atoms and the like.

The crosslinking agent represented by the formula [V] specifically includes N-hydroxysuccinimide ester of m-maleimidobenzoic acid

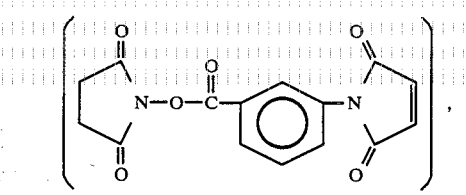

N-hydroxysuccinimide ester of N-(4-carboxycyclohexylmethyl)maleimide

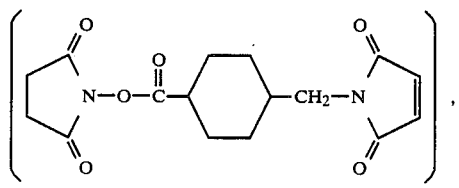

N-hydroxysuccinimide ester of N-(4-carboxyphenylmethyl)maleimide

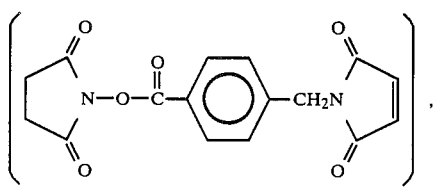

N-(ε-maleimidocaproxy)succinimide

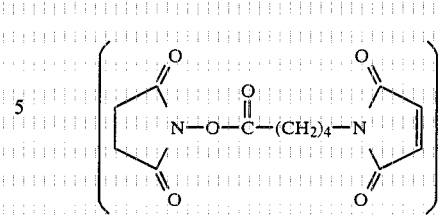

and the like.

The crosslinking agent having a functional group represented by the formula —$CH_2L$ includes N-hydroxysuccinimide ester of iodoacetic acid In the above-mentioned first, second, third and fourth methods, the reaction of the amino group of a biologically active protein and a crosslinking agent can be conducted as follows:

To a buffer solution having a pH of 5–9 in which a biologically active protein is dissolved at a concentration of 0.5–100 mg/ml, preferably 1–20 mg/ml, is added a crosslinking agent in a proportion of 1–100 mols per mol of the biologically active protein, and the reaction is carried out with stirring at 0°–50° C.

The reaction time may vary depending on the reaction scale and reaction conditions, and is usually within 2 days. The crosslinking agent is used as an aqueous solution, or if it is insoluble in water, it is used as a solution in a small amount of an organic solvent such as DMF, DMSO, 1,2-dimethoxyethane, 1,4-dioxane, methanol, ethanol, acetone or the like.

After completion of the reaction, the product can be purified by removing lower molecular weight substances by a usual means such as dialysis, gel-filtration or the like.

The reaction for combining a biologically active protein having a mercapto group or the protein having introduced thereinto a mercapto group with a polysuccinimide derivative of the thiol type using a bifunctional crosslinking agent in the said third method can also be conducted in the same way as above.

In the final reaction for obtaining a proteinpolysuccinimide complex in the above-mentioned first to fourth methods, a biologically active protein, a biologically active protein having a mercapto group introduced through a crosslinking group or a modification thereof (hereinafter these are collectively referred to as a reactive biologically active protein) and the above-mentioned polysuccinimide derivative [I] are reacted as follows in an appropriate combination as explained in the above-mentioned first to fourth methods:

A buffer solution having a pH of 5–9 having dissolved therein a reactive biologically active protein at a concentration of 0.5–100 mg/ml, preferably 1–20 mg/ml and an aqueous solution of a polysuccinimide derivative [I] or the same buffer solution as above having dissolved therein a polysuccinimide derivative [I], said derivative [I] being to be combined with said reactive biologically active protein, and mixed and allowed to stand at 0°–50° C. or stirred slowly to effect reaction. The polysuccinimide derivative [I] is used in a proportion of 0.1–70 moles per mole of the biologically active protein. The reaction time is usually within 3 days.

Separation and purification of the objective complex from the reaction mixture can be carried out by usual methods such as gel-filtration, affinity chromatography, dialysis, precipitation and the like.

The complex of this invention thus obtained can be labelled with a radio-metal ions according to well-known general methods.

REFERENCE EXAMPLE 1

Polymerization of Polysuccinimide

To 66.5 g of L-aspartic acid was added 20.6 ml of 85% phosphoric acid, and the resulting mixture was subjected to polymerization at a reduced pressure of 10 mmHg for 5.5 hours while heating the mixture at 190° C. by a rotary evaporator.

The polymerization product was dissolved in DMF and then reprecipitated in water. The precipitate was separated by filtration through a glass filter and then dried at 80° C. in vacuo for 3 days.

The polymer thus obtained was subjected to measurement of infrared absorption by a KBr tablet method to confirm absorptions characteristic of succinimide group at 1800, 1720 and 1660 cm$^{-1}$. The $^{13}$C-NMR data of the polymer were as follows:

172.28 ( =O), 173.54 (C=O), 32.64 (CH$_2$), 47.50 (CH) ppm,

The measurement of the molecular weight of the polymer was conducted by GPC. Using a GPC column for DMF (AD-80 M/S, Showa Denko), the polysuccinimide thus obtained was dissolved in a DMF +0.01M LiBr solvent at a concentration of 0.2%, and 250 $\mu$l of the resulting solution was poured into the column. The measurement was conducted by means of a differential refractometer using the same solvent as an eluent. A calibration curve was prepared using polyethylene glycol having various molecular weights. The polysuccinimide obtained had a polyethylene glycol-reduced weight mean molecular weight of $8.9 \times 10^4$ and a number average molecular weight of $1.5 \times 10^4$.

REFERENCE EXAMPLE 2

Method for Producing Immunoglobulin

A method for producing a monoclonal antibody to human transferrin receptor is described in Omary, M. B., al., Nature 286 888 (1980).

Spleen lymphocyte of a BALB/C strain mouse immunized with a K562 strain obtained from a human chronic myelocytic leukemia patient and 8194/5XX0. BU 1 strain which is an immunoglobulin-unproducing myeloma cell were subjected to cell fusion is a conventional manner, and a hybridoma producing an antibody to transferrin receptor was selected.

The above hybridoma was injected into a BALB/C strain mouse to which pristane had previously been administered, and after about two weeks, ascites fluid was collected.

Immunoglobulin was purified from the ascites fluid. The ascites fluid was precipitated from 50% saturated aqueous ammonium sulfate solution, and the precipitate was dissolved in sodium phosphate buffer, after which the resulting solution was subjected to dialysis and then to DEAE-ion exchange column to obtain a IgG fraction. This fraction was further concentrated using an Amicon membrane (manufactured by Amicon, PM-10) to obtain a solution having a protein concentration of 5 mg/ml.

EXAMPLE 1

In 3.0 ml of DMSO was dissolved 500 mg of the polysuccinimide obtained in Reference Example 1 (corresponding to 5.16 mols of succinimide group), and to the resulting solution was added 2530 mg (3.85 mmols) of deferoxamine mesylate (Desferal, a trademark of Bayer), after which 4.62 mmols of triethylamine was added thereto. The resulting mixture was stirred at 60° C. for 4 hours, and a mixture of 16.6 mmols of cysteamine and 16.75 mmols of ethanolamine with 5 ml of DMSO was added thereto. The resulting mixture was subjected to reaction at 60° C. for one hour. The reaction mixture was allowed to stand overnight, placed in a dialysis tube, and subjected to dialysis to water for 2 days, and then freeze-dried. The polysuccinimide derivative thus obtained was dissolved in water, and the resulting solution was subjected to gel filtration using Sephadex ® G-50 (manufactured by Pharmacia) to separate a fraction having a globular protein-reduced average molecular weight of 20,000, which was freeze-dried. No unreacted succinimide group was detected by measurement of IR and $^{13}$C-NMR. The amount of deferoxamine introduced was determined by the following method:

400 $\mu$l of the reaction mixture after the reaction but before dialysis was measured, and 400 $\mu$Ci of $^{67}$Ga-citrate solution was added thereto, and the resulting mixture was allowed to stand for 5 hours to chelate $^{67}$Ga to deferoxamine. This reaction mixture was thereafter subjected to separation by cellulose acetate membrane electrophoresis and then to measurement of radioactivity. The deferoxamine introduced into the reactive high polymer and unreacted deferoxamine were completely separated. The radioactivity corresponding to the deferoxamine introduced into the reactive high polymer was 73% based on the total radioactivity.

The amount of the deferoxamine introduced per mol of succinimide group was determined by the following equation:

(Mols of deferoxamine mesylate charged)×(ratio of radioactivity introduced into the reactive high polymer)/(mols of succinimide group charged)=$3.85 \times 0.73/5.16 = 0.54$ (mol)

That is, 0.54 mol of deferoxamine was introduced per mol of succinimide group.

The amount of thiol group was determined by elementary analysis of sulfur. The elementary analysis value of sulfur was 0.54% by weight.

The direct determination of thiol group was conducted based on the method described in Anal. Biochem. 25, 192 (1968), namely the DTNB 5,5-dithiobis(2-nitrobenzoic acid) method.

In 1 ml of 8M urea solution was dissolved 20 mg of polysuccinimide derivative, and to the resulting solution were added 0.1 ml of 0.1M EDTA, 1 ml of 2.5% aqueous NaBH$_4$ solution and 1 ml of distilled water, after which one drop of n-octanol was dropped thereinto. The resulting mixture was subjected to reaction at 38° C. for 30 minutes, to reduce the disulfide linkage formed in equilibrium in the polysuccinimide derivative, and thereafter, 0.5 ml of 1M KH$_2$PO$_4$-0.2N HCl was added thereto in order to remove the exessive NaBH$_4$. After five minutes, 2 ml of acetone was added, and a nitrogen gas was bubbled through the resulting mixture for five minutes. To the mixture was added 0.5 ml of 0.01M 5,5'-dithiobis(2-nitrobenzoic acid), and subjected to measurement of absorbance at 412 nm after 15 minutes, thereby determining the amount of thiol group. The result of measurement was substantially identical with the elementary analysis value.

The molecular weight was determined by measuring the terminal amine. In 1 ml of 0.1M sodium borate solution (pH 9.2) was dissolved 5 mg of the above intermediate, and then 0.1 ml of a solution of 32 mg of 2,4,6-trinitrobenzenesulfonic acid (referred to as TNBS hereinafter) in 10 ml of 0.1M sodium borate solution was added thereto, after which the resulting mixture was subjected to reaction at 25° C. for 45 minutes. Further, 1.9 ml of 0.1M sodium borate solution was added, and the resulting mixture was subjected to measurement of absorbance at 420 nm. From a calibration curve obtained using known amounts of aspartic acid, a molecular extinction coefficient of 11,100 was obtained, and the value of the terminal amine was calculated using the molecular extinction coefficient to find that $1.1 \times 10^{-4}$ mol of amino group was present in 1 g of the polysuccinimide derivative and the mean molecular weight thereof was 9,000.

EXAMPLE 2

In 3.0 ml of DMSO was dissolved 500 mg of the polysuccinimide obtained in Reference Example 1 (corresponding to 5.16 mmols of succinimide group), and to the resulting solution was added 2,530 mg (3.85 mmols) of deferoxamine mesylate, after which 4.62 mmols of triethylamine was added thereto. The resulting mixture was stirred at 60° C. for 4 hours, and thereafter, a mixture of 0.67 mmol of cysteamine and 16.75 mmols of ethanolamine with 5 ml of DMSO was added thereto. The resulting mixture was further subjected to reaction at 60° C. for 1 hour. The reaction mixture was allowed to stand overnight, then placed in a dialysis tube, and subjected to dialysis to water for 2 days, and thereafter freeze-dried.

The polysuccinimide derivative thus obtained was dissolved in water and the resulting solution was subjected to gel filtration using Sephadex G-50 to collect a fraction having a globular protein reduced mean molecular weight of 20,000, which was then freeze-dried. No unreacted succinimide group was detected by the measurement of IR and $^{13}$C-NMR.

In the same manner as in Example 1, the amounts of the deferoxamine and cysteamine introduced per mol of succinimide group were determined. The results were 0.55 mol of deferoxamine and 0.02 mol of cysteamine.

In the same manner as in Example 1, the molecular weight was determined to be 9,000.

EXAMPLE 3

In 3.0 ml of DMSO was dissolved 500 mg of the polysuccinimide obtained in Reference Example 1, and to the resulting solution was added 960 mg (1.47 mmols) of deferoxamine mesylate. The resulting mixture was subjected to reaction at room temperature for 24 hours, and thereafter 1.20 mmols of n-propyl-2-aminoethyl disulfide was added thereto, and the resulting mixture was subjected to reaction at room temperature for 6 hours, after which 10 mmols of 3-amino-1,2-propandiamine was added. The resulting mixture was subjected to reaction at room temperature for 12 hours. After the reaction, the reaction mixture was placed in a dialysis tube and subjected to dialysis to water for 2 days, and thereafter freeze-dired. In 6.0 ml of 0.1M tris-hydrochloric acid-1 mM EDTA buffer (pH 8.45) was dissolved 200 mg of the polysuccinimide derivative thus obtained, and to the resulting solution was added a solution of 0.02M dithiothreitol in 2.0 ml of the same buffer, and the resulting mixture was subjected to reduction reaction at 50° C. for 100 minutes. The reaction mixture was subjected to gel filtration using Sephadex G-50 to separate a fraction having a globular protein-reduced mean molecular weight of 100,000, which was then freeze-dried.

In the same manner as in Example 1, the amount of deferoxamine introduced per mol of succinimide group and the amount of thiol group introduced were measured to find that 0.25 mole of deferoxamine was introduced per mol of succinimide group and 0.20 mol of thiol group was introduced.

In the same manner as in Example 1, the mean molecular weight was determined to be 50,000.

EXAMPLE 4

In 5 ml of 8M urea solution was dissolved 28 mg of the thiol type reactive high polymer obtained in Example 1, and 4.85 mg of dithiothreitol was added thereto, after which the resulting mixture was subjected to reaction at 37° C. for one hour. To the reaction mixture was added a solution of 16.07 mg of 5,5'-dithiobis(2-nitrobenzoic acid) in 0.15 ml of ethanol, and the resulting mixture was subjected to reaction at room temperature for one hour, after which the reaction mixture was subjected to gel filtration using Sephadex G-25 to remove the low molecular weight fractions, thereby obtaining a high molecular weight fraction, which was then freeze-dried.

In order to confirm that the thiol group of the reactive high polymer having active disulfide linkage thus obtained had been converted into active disulfide linkage, the high molecular weight fraction was dissolved again in 5 ml of 8M urea solution, and 4.85 mg of dithiothreitol, after which the resulting mixture was subjected to reaction at 37° C. for one hour. The amount of active disulfide linkage was determined by measurement of absorbance at 412 nm. The result of measurement indicated that almost all thiol group was converted into active disulfide linkage.

EXAMPLE 5

To 10 ml of distilled water was added 1055 mg of Fibrinogen-Midori (obtained from The Green Cross Corporation) (330 mg of fibrinogen), and the resulting mixture was stirred at room temperature for 30 minutes to obtain a solution. To this solution were added 121 mg of dimethyl-3,3'-dithiobispropionimidate hydrochloride (obtained from Pierce) and a solution of 60 mg of dithiothreitol in 6 ml of distilled water, and the resulting mixture was subjected to reaction at 23° C. for 40 minutes. Using a column having a size of 2.6 cm$\phi \times$40 cm of Sephadex G-25 superfine (manufactured by Pharmacia) equilibrated with 0.01M phosphate-buffered physiological saline (PBS) having a pH of 8.0, the reaction mixture was subjected to gel filtration to remove the low molecular weight fraction. To the remaining fraction was added 32 mg of the reactive high polymer which was obtained by subjecting the reactive high polymer having active disulfide linkage (obtained in Example 4) to gel filtration using a column having a size of 2.6 cm$\phi \times$20 cm of Sephadex G-25 equilibrated with the same buffer to remove the low molecular weight fraction and freeze-drying the residue, and the resulting mixture was subjected to reaction at 4° C. for 18 hours. After the reaction, the reaction mixture was subjected to gel filtration using a column of 2.6 cmφ×100 cm of Sepharose CL-6B (manufactured by Pharmacia) equilibrated with the same buffer to separate the fibrinogen fraction. The protein recovery was about 20%.

In order to confirm that the coagulation ability of the fibrinogen obtained did not change, the coagulation ability was measured according to the method described in Arch. Biochem. Biophys. 32 (1951) 317–324. An aqueous solution of the complex was prepared so that the concentration of the fibrinogen in the complex was 0.56 mg/ml, and to 45 ml of this solution was added 0.5 ml of the same buffer containing 50 units/ml of thrombin, after which the resulting mixture was allowed to stand at room temperature for one hour. The resulting clot was removed, and the fibrinogen concentration of the remaining solution was determined by measuring the absorbance at 280 nm, from which the coagulation percentage of fibrinogen was calculated. The coagulation percentage was 85%. The coagulation percentage of the fibrinogen used was 86%, and hence, it was confirmed that even when the fibrinogen formed a complex the coagulation ability of the fibrinogen did not reduce.

To an aqueous solution containing 0.45 mCi of gallium-67 citrate solution was added 1 ml of an aqueous solution of 0.56 mg/ml of the complex, and the resulting mixture was allowed to stand for one hour. The reaction mixture was subjected to separation by a cellulose acetate electrophoresis, whereby it was confirmed that no unlabelled $^{67}$Ga was present. From this fact, it was confirmed that the labelled complex having a specific radioactivity of at least 0.8 mCi/mg of fibrinogen was obtained and that the reactive high polymer was bound to the fibrinogen.

EXAMPLE 6

A buffer solution corresponding to 31 mg of the immunoglobulin obtained in Reference Example 2 was subjected to buffer exchange by means of Sephadex G-25 equilibrated with 0.1M phosphate buffer (pH of 7.0) containing 1 mM EDTA and then concentrated to 5 mg/ml using an Amicon membrane (PM-10). To 6 ml of the solution thus obtained was added 30 μl of a solution of 40 mM N-hydrosuccinimide ester of 5-(4-carboxycyclohexylmethyl)maleimide in dioxane, and the resulting mixture was subjected to reaction at 30° C. for one hour. After the reaction, the reaction mixture was subjected to gel filtration using a column having a size of 2.0 cmφ×20 cm of Sephadex G-25 superfine equilibrated with the same buffer to remove the low molecular weight fraction.

In 3 ml of the same buffer was dissolved 30 mg of the reactive polymer obtained in Example 1, and to the resulting solution was added 13 mg of dithiothreitol. The resulting mixture was subjected to reaction at 30° C. for 2 hours, after which the reaction mixture was subjected to gel filtration in the same manner as above to remove the low molecular weight fraction.

The two remaining solutions obtained by the above gel filtration were mixed together, and the resulting mixture was allowed to stand at 4° C. for 18 hours to effect reaction. For the purpose of removing the unreacted reactive high polymer, the reaction mixture was subjected to column of 30 ml of Protein A column (manufactured by Pharmacia) equilibrated with 0.1M phosphate buffer having a pH of 8.20, and then, the unadsorbed fraction was sufficiently removed by means of an equilibrated buffer, after which the Protein A column adsorbed fraction was eluted with 0.58% acetic acid-0.15N NaCl solution. The eluate was subjected to dialysis to 1 liter of 0.1M carbonate/bicarbonate buffer having a pH of 9.3, after which the dialyzed solution was concentrated through an Amicon membrane (PM-10) to obtain 6 ml of a solution having a protein concentration of 1.13 mg/ml.

In order to confirm that the complex thus obtained was a conjugate of the immunoglobulin and the reactive high polymer, the concentrated solution was labelled with $^{67}$Ga in the same manner as in Example 1. To the concentrated solution was added 0.90 ml of a solution containing 0.90 mCi of gallium-67 citrate, and the resulting mixture was allowed to stand for one hour. The reaction mixture thus obtained was subjected to separation by means of cellulose acetate electrophoresis, whereby it was confirmed that no unlabelled gallium-67 was present. From this fact, it was confirmed that the complex can be labelled at a specific radioactivity of at least 0.8 mCi/mg immunoglobulin, and the immunoglobulin was bound to the reactive high polymer.

In order to confirm that the immunoglobulin of the complex had a binding ability to an antigen, the following experiment was conducted:

The immunoglobulin was labelled with iodide by the Chloramine-T method. To a plastic tube were added 5 μl of 0.5M sodium phosphate buffer having a pH of 7.5 (referred to hereinafter as the buffer) and 0.3 mCi of Na$^{125}$I, and the resulting mixture was stirred, after which 20 μl of a solution of 200 μg/ml of Chloramine-T in the buffer was added thereto. The resulting mixture was stirred for 20 seconds, and thereto was added 20 μl of a solution of 0.5 mg/ml of immunoglobulin in the buffer, after which the resulting mixture was stirred for 15 seconds to conduct reaction. After the reaction, 400 μl of a solution of 14 μg/ml of Na in the buffer, 25 μl of a solution of 20 mg/ml of KI in the buffer and 25 μl of a solution of 5% BSA in the buffer were added, after whcih the resulting mixture was subjected to gel filtration in a Sephadex G-25 column using the buffer as an eluent to separate the protein eluate and remove the low molecular weight fraction. The specific radioactivity of $^{125}$I-labelled immunogloblin was determined by determining the protein concentration from the absorbance at 280 nm and measuring the total radioactivity. The specific radioactivity was 4.3 mCi/mg. The above $^{125}$I-labelled immunogloblin having a radioactivity of 2×10$^5$ cpm was added to 1 ml of 10% FCS-RPM1-1640 medium (obtained from Nakarai Chemical), and to 0.1 ml of the resulting solution was added 0.4 ml of RPM1-1640 medium solution of 1.0–0.1 mg/ml of the above complex, after which to the resulting solution was added 0.5 ml of 10% FCS-RPM1-1649 medium of 1×10$^6$ cells/ml of CCRF-CEM cell which is known to have a human transferrin receptor. The resulting mixture was subjected to incubation at 4° C. for one hour. Thereafter, the resulting mixture was subjected to centrifugation at 2,000 rpm for five minutes, and the supernatant was wasted. To the residue was added 0.5% BSA-Hanks buffer, and the resulting mixture was subjected to centrifugation at 2,000 rpm for five minutes. The supernatant was wasted and the radioactivity of the residue was measured.

For comparison, another experiment was conducted by adding immunoglobulin instead of the complex. It was found that the inhibition effect of the complex against the binding of the $^{125}$I-labelled immunoglobulin to CCRF-CEM cells was the same as that of the immunoglobulin at the same concentration, and the immunoglobulin of the complexes had the same binding ability as that of the original immunoglobulin.

EXAMPLE 7

In the same manner as in Example 6, the immunoglobulin obtained in Reference Example 2 was exchanged with 0.1M phosphate buffer (pH 7.0) containing 1 mM EDTA and concentrated through an Amicon membrane to 5.5 mg/ml. To 6 ml of the thus obtained solution was added 30 μl of an ethanol solution of 20 mM N-succinimidyl-3-(2-pyrimidylthio)propionate, and the resulting mixture was subjected to incubation at 23° C. for 30 minutes. After the reaction, 5 mg of glycine as a reaction terminator and 5 mg of dithiothreitol as a reducing agent were added thereto, and the resulting mixture was subjected to incubation at 23° C. for 30 minutes. Thereafter, the resulting mixture was subjected to gel filtration using a column having a size of 2 cm$\phi$×20 cm of Sephadex G-25 equilibrated with the same buffer to remove the low molecular weight fraction and obtain 7 ml of the protein fraction.

To the protein fraction was added 10 mg of the reactive high polymer having active disulfide linkage obtained in Example 4, and the resulting mixture was subjected to incubation at 4° C. for 18 hours, after which it was subjected to separation in a Protein A column and then to concentration in the same manner as in Example 6, to obtain about 6 ml of a solution having a protein concentration of 1.12 mg/ml.

Under the same conditions as in Example 6, the concentrated solution was labelled with gallium-67 and subjected to separation. It was found that no unlabelled gallium-67 was present, a complex having a specific radio-activity of at least 0.8 mCi/mg immunoglobulin was formed, and the immunoglobulin was bound to the reactive high polymer.

The confirmation of the maintenance of the binding ability to an antigen of the immunoglobulin as an antibody in the complex was conducted by comparing the inhibition effect of $^{125}$I-labelled immunoglobulin against the binding to an antigen with that of the original immunoglobulin, and it was confirmed that the binding ability did not reduce.

EXAMPLE 8

In 40 ml of 0.1M acetic acid buffer having a pH of 4.5 was dissolved 1.2 g of immunoglobulin, and 24 mg of pepsin was added to the resulting solution, after which the resulting mixture was subjected to decomposition at 37° C. for about 18 hours. The decomposition product was subjected to a column having a size of 3.5 cm$\phi$×140 cm of Sephadex G-200 (manufactured by Pharmacia) in physiological saline, and proteins in the fraction having a molecular weight of about 100,000 were collected to obtain F(ab')$_2$.

To 1.14 ml of 10 mM phosphate buffer having a pH of 6.5 containing 10 mg of F(ab')$_2$ was added 0.05 ml of N,N-dimethylformamide containing 0.42 mg of N-hydroxysuccinimidyl-m-maleimidobenzoic acid, and the resulting mixture was subjected to reaction at room temperature for 40 minutes. After the reaction, the reaction mixture was subjected to dialysis using 5 mM acetic acid buffer containing 0.14M sodium chloride and 1 mM EDTA to remove the excessive reagent and obtain m-maleimidobenzoyl F(ab')$_2$.

In 3 ml of a buffer of 0.1M phosphate-1 mM EDTA having a pH of 7.0 was dissolved 41 mg of the reactive high polymer obtained in Example 1, and to the resulting solution was added 13 mg of dithiothreitol, after which the resulting mixture was subjected to reaction at 30° C. for 2 hours. Thereafter, the reaction mixture was subjected to gel filtration using a column having a size of 2.0 cm$\phi$×13.5 cm of Sephadex G-25 superfine equilibrated with 5 mM acetic acid buffer having a pH of 5.5 containing 0.14M sodium chloride and 1 mM EDTA to remove the low molecular weight fraction.

A buffer corresponding to 30 mg of m-maleimidobenzoyl F(ab')$_2$ was mixed with a buffer corresponding to 15 mg of the reactive high polymer, and 0.3 ml of 0.5M phosphate buffer having a pH of 6.5 was added to the resulting mixture, after which the mixture was subjected to reaction at 4° C. for 16 hours. After the reaction, the reaction mixture was subjected to dialysis to 0.9% sodium chloride solution.

The complex thus obtained was concentrated to an immunoglobulin concentration of 1.1 mg/ml, and to 1 ml of the concentrated solution was added 4 mCi of $^{67}$Ga-citrate solution, and the mixture was allowed to stand for one hour. The reaction mixture thus obtained was subjected to separation by cellulose acetate electrophoresis to confirm that no unlabelled gallium was present.

To 0.5 ml of each of the various diluted solution of 10$^6$ cells/ml of CCRF-CEM cell or FM-3A cell having no human transferrin receptor was added 0.4 ml of a solution of 5×10$^4$ cpm of the $^{67}$Ga-labelled complex in 1 ml of 10% FCS-RPM1-1640 medium, and the resulting mixture was subjected to incubation at 4° C. for one hour, after which the incubated mixture was subjected to centrifugation at 2,000 rpm for five minutes. The supernatant was wasted, and to the residue was added 0.5 ml of 0.5% BSA-Hank's solution to wash the residue, after which the resulting mixture was subjected to centrifugation at 2,000 rpm for five minutes. The supernatant was wasted, and the radioactivity of the residue was measured using γ-counter. The results obtained are shown in Table 1.

TABLE 1

| | Cell | |
|---|---|---|
| Dilution degree | CCRF-CEM | FM-3A |
| 1 | 3 × 10$^3$ cpm | 0.1 × 10$^3$ cpm |
| 1/4 | 1 × 10$^3$ cpm | 0.1 × 10$^3$ cpm |
| 1/16 | 0.5 × 10$^3$ cpm | 0.1 × 10$^3$ cpm |
| 1/64 | 0.2 × 10$^3$ cpm | 0.1 × 10$^3$ cpm |

From the above results, it was confirmed that a complex was synthesized and the binding ability of F(ab')$_2$ to an antigen was maintained.

EXAMPLE 9

In the same manner as in Example 8, F(ab')$_2$ was obtained by decomposing immunogloblin with pepsin. To 3.43 ml of 0.1M phosphate-1 mM EDTA (pH 6.0) buffer containing 40 mg of F(ab')$_2$ was added 1 ml of a solution of 2-mercaptoethylamine in the same buffer, and the resulting mixture was reduced at 37° C. for 90 minutes, after which the resulting solution was subjected to gel filtration using Sephadex G-25 equilibrated with the same buffer to remove the low molecular weight fraction. A protein fraction was collected, and 25.7 ml of a saturated solution of N,N-o-phenylenedimaleimide in 0.1M acetic acid-1 mM EDTA buffer having a pH of 5.0 was added thereto, after which the resulting mixture was subjected to reaction at 30° C. for 20 minutes with stirring. After the reaction, the reaction mixture was subjected to gel filtration using Sephadex G-25 equilibrated with 0.02M acetic acid buffer having a pH of 5.0 to remove the low molecular weight fraction, and the residue was concentrated to obtain a solution having a concentration of 2.5 mg/ml of Fab' having maleimide group introduced thereinto.

In 3 ml of a 0.1M phasphate-1 mM EDTA buffer having a pH of 7.0 was dissolved 41 mg of the reactive high polymer obtained in Example 1, and to the resulting solution was added 13 mg of dithiothreitol, after which the resulting mixture was subjected to reaction at 30° C. for 2 hours. After the reaction, the reaction mixture was subjected to gel filtration using Sephadex G-25 equilibrated with 5 mM acetic acid buffer (pH 5.5) conteining 0.14M sodium chloride-1 mM EDTA to remove the low molecular weight.

A buffer corresponding to 15 mg of Fab' having maleimide group introduced was mixed with a buffer corresponding to 15 mg of the reactive high polymer, and 0.3 ml of 0.5M phosphate buffer (pH 6.5) was added to the resulting mixture. The mixture was subjected to reaction at 4° C. for 16 hours. After the reaction, the reaction mixture was subjected to dialysis to 0.9% sodium chloride solution.

A complex was obtained in the same manner as in Example 8, labelled with $^{67}$Ga, and thereafter subjected to examination of the binding ability to CCRF-CEM cell and FM-3A cells to obtain the data shown in Table 2.

TABLE 2

| Degree of dilution | Cell | |
|---|---|---|
| | CCRF-CEM | FM-3A |
| 1 | $2 \times 10^3$ cpm | $0.05 \times 10^3$ cpm |
| 1/4 | $0.8 \times 10^3$ cpm | $0.05 \times 10^3$ cpm |
| 1/16 | $0.3 \times 10^3$ cpm | $0.05 \times 10^3$ cpm |
| 1/32 | $0.1 \times 10^3$ cpm | $0.05 \times 10^3$ cpm |

From the above results, it was confirmed that a complex was synthesized and the binding ability of Fab' to an antigen was maintained.

TEST EXAMPLE

Distribution in Rat Body of Protein-Polysuccinimide Complex Labelled with Gallium-67

To 2 ml of a solution containing 2 mCi of gallium-67 citrate was added 20 mg of the protein-polysuccinimide complex prepared in the same manner as in Example 6, and the resulting mixture was allowed to stand for one hour, thereby obtaining a gallium-67 labelled protein-polysuccinimide complex. It was confirmed by cellulose acetate electrophresis that there was not present any unlabelled gallium-67. 0.2 ml of this gallium-67 labelled protein-polysuccinimide complex was measured, and intravenously administered to three S.D. strain female rats. In one hour after the administration, each organ was enucleated from the rat and subjected to measurement of radioactivity, to determine the percentage of the complex taken in each organ. The results are shown in Table 3.

TABLE 3

| Organ | Percentage of complex taken in |
|---|---|
| Blood | 75 |
| Liver | 7 |
| Kidney | 5 |
| Lung | 2 |
| Spleen | 0.5 |
| Large intestine | 2 |
| Small intestine | 2 |
| Stomach | 0.5 |
| Urine | 5 |

As is clear from the above results, it was confirmed that the labelled complex was useful as a noninvasive nuclear medicine diagnostic.

What is claimed is:

1. A protein-polysuccinimide complex wherein a biologically active protein is combined with a polysuccinimide [I] having a mean molecular weight of 2,000 to 1,000,000 and consisting of constitutive units represented by the formulae:

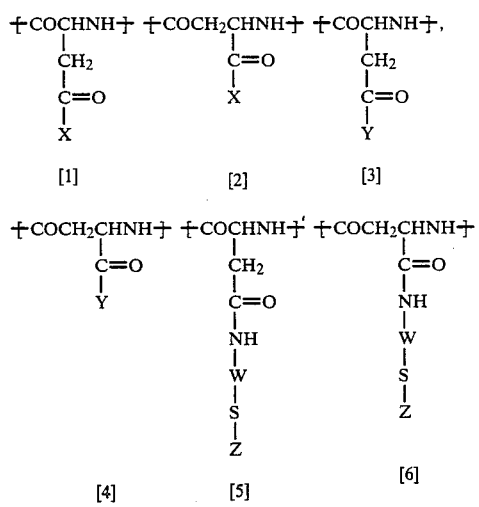

wherein
X represents a residue of a bifunctional chelate having an amino group in the molecule;
Y represents a water soluble aliphatic primary amine residue;
W represents a lower alkylene group;
Z represents a hydrogen atom or a group represented by the symbol Z', provided that when Z is a hydrogen atom, the —SH group represented by —SZ may intramolecularly or intermolecularly form a —S—S— bond with another —SH group in equilibrium; and these are also represented by —SH; and
Z' represents a group which can form an active disulfide bond with the adjacent sulfur atom, the numbers of the respective constitutive units represented by the formula [1], [2], [3], [4], [5] and [6] in one molecule being n, m, l, r, p and q, respectively, which denote 0 or natural numbers and have the following relationships;

$n + m \geqq 2$ $0.001 \leqq (p+q)/(n+m+l+r+p+q) \leqq 0.50.$

2. A protein-polysuccinimide complex according to claim 1, wherein the combination between the polysuccinimide derivative [I] and the biologically active protein is a disulfide bond which is formed by utilization of the —SZ group of the polysuccinimide derivative [I] and the mercapto group of the biologically active protein.

3. A protein-polysuccinimide complex according to claim 1, wherein the combination between the polysuccinimide derivative [I] and the biologically active protein is formed by utilization of the —SZ group of the polysuccinimide derivative [I] and the amino group of the biologically active protein and through a crosslinking group therebetween.

4. A protein-polysuccinimide complex according to claim 1, wherein the combination between the polysuccinimide derivative [I] and the biologically active protein is formed by utilization of the —SZ group of the polysuccinimide derivative [I] and the mercapto group of the biologically active protein having a mercapto group and through a crosslinking group therebetween.

5. A protein-polysuccinimide complex according to claim 1, wherein the biologically active protein is fibrinogen, urokinase, plasminogen, albumin or immunoglobulin.

6. A process for preparing a protein-polysuccinimide complex as claimed in claim 1, which comprises reacting a biologically active protein having a mercapto group or a biologically active protein having a mercapto group introduced into its amino group through a crosslinking group with a polysuccinimide derivative [I] in which Z=Z'.

7. A process for preparing a protein-polysuccinimide complex as claimed in claim 1, which comprises introducing a Z' group into the mercapto group of a biologically active protein having a mercapto group to form a —SZ' group, or introducing a —SZ' group into the amino group of a biologically active protein through a crosslinking group, and then reacting the thus obtained biologically active protein having a —SZ' group or having a —SZ' group introduced through a crosslinking group with the polysuccinimide derivative [I].

8. A process for preparing a protein-polysuccinimide derivative as claimed in claim 1, which comprises reacting one of the biologically active protein having a mercapto group or the biologically active protein having a mercapto group introduced into its amino group through a crosslinking group and the polysuccinimide derivative [I] in which Z is a hydrogen atom with a crosslinking agent in excess of the mercapto group included, and then reacting the reaction product with the other.

9. A process for preparing a protein-polysuccinimide complex as claimed in claim 1, which comprises reacting a polysuccinimide derivative [I] wherein Z is a hydrogen atom with a biologically active protein having a functional group which can react with a mercapto group, introduced into the amino group through a crosslinking group.

10. A polysuccinimide derivative having a mean molecular weight of 2,000 to 1,000,000 and consisting of constitutive units represented by the formulae:

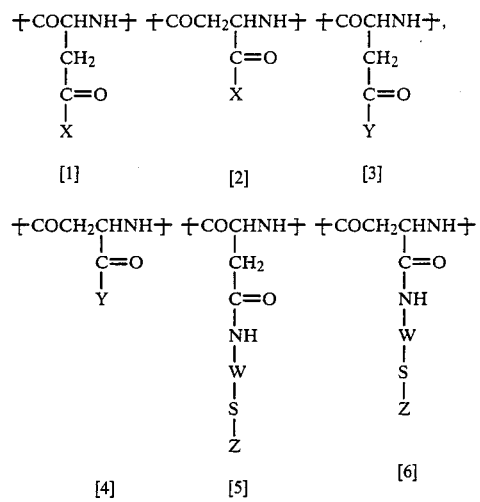

wherein
X represents a residue of a bifunctional chelate having an amino group in the molecule;
Y represents a water soluble aliphatic primary amine residue;
W represents a lower alkylene group;
Z represents a hydrogen atom or a group represented by the symbol Z', provided that when Z is a hydrogen atom, the —SH group represented by —SZ may intermolecularly or intramolecularly form a —S—S— bond with another —SH group in equilibrium and these are also represented by —SH; and
Z' represents a group which can form an active disulfide bond with the adjacent sulfur atom, the numbers of the respective constitutive units [1], [2], [3], [4], [5] and [6] in one molecule being n, m, l, r, p and q, respectively, which denote 0 or natural numbers and have the following relationships:

$n + m \geq 2$ $0.001 \leq (p+q)/(n+m+l+r+p+q) \leq 0.50.$

11. A process for preparing a polysuccinimide derivative as claimed in claim 10, which comprises reacting a polysuccinimide having recurring units represented by the formula,

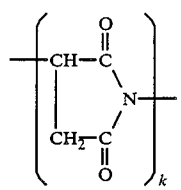

wherein k represents a natural number, with
(a) a bifunctional chelate having an amino group,
(b) a compound represented by the formula H$_2$N—W—S—Z, wherein W and Z have the same meanings as defined in claim 10, and
(c) if necessary, a water soluble aliphatic primary amine.

12. A process for preparing a polysuccinimide derivative as claimed in claim 10, wherein Z is a hydrogen atom, which comprises reacting a polysuccinimide having recurring units represented by the formula,

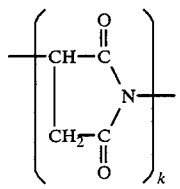

wherein k represents a natural number, with (a) a bifunctional chelate having an amino group,
(b) a compound represented by the formula $H_2N-W-S-S-R$, wherein W has the same meaning as defined in claim 10, and
(c) if necessary, a water soluble aliphatic primary amine, and then reductively splitting the disulfide bond of the resulting reaction product.

13. A process for preparing a polysuccinimide derivative as claimed in claim 10 wherein $Z=Z'$, which comprises reacting an active disulfide compound with a polysuccinimide derivative as claimed in claim 10 wherein Z is a hydrogen atom.

* * * * *